US008399017B2

(12) United States Patent
Joanny

(10) Patent No.: US 8,399,017 B2
(45) Date of Patent: *Mar. 19, 2013

(54) USE OF A MATRIX FOR ORALLY ADMINISTERING SUSTAINED RELEASE MAGNESIUM, AND COMPOSITION CONTAINING SAID MATRIX

(76) Inventor: Fabienne Joanny, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 12/993,678

(22) PCT Filed: May 20, 2009

(86) PCT No.: PCT/FR2009/000585
§ 371 (c)(1),
(2), (4) Date: Nov. 19, 2010

(87) PCT Pub. No.: WO2009/150323
PCT Pub. Date: Dec. 17, 2009

(65) Prior Publication Data
US 2011/0091548 A1 Apr. 21, 2011

(30) Foreign Application Priority Data
May 20, 2008 (FR) .................................... 08 02702

(51) Int. Cl.
A61K 9/22 (2006.01)
(52) U.S. Cl. ........ 424/480; 424/464; 424/465; 424/479; 424/481
(58) Field of Classification Search ........... 424/464–489
See application file for complete search history.

(56) References Cited

U.S. PATENT DOCUMENTS

| 4,810,496 | A | 3/1989 | Jensen |
| 5,068,112 | A | 11/1991 | Samejima et al. |
| 5,135,850 | A | 8/1992 | Prost |
| 5,849,338 | A | 12/1998 | Richardson et al. |
| 5,898,037 | A * | 4/1999 | Marx ............................... 424/49 |
| 5,976,568 | A | 11/1999 | Riley |
| 6,887,492 | B2 | 5/2005 | Kay et al. |
| 2004/0156896 | A1 | 8/2004 | Dixit et al. |
| 2005/0220865 | A1 | 10/2005 | Koleng et al. |
| 2005/0266082 | A1 | 12/2005 | Patel et al. |
| 2006/0217385 | A1 | 9/2006 | Edwards et al. |
| 2006/0257483 | A1* | 11/2006 | Yang et al. ..................... 424/471 |
| 2008/0031904 | A1 | 2/2008 | Menvielle-Bourg-Joanny |
| 2011/0097400 | A1 | 4/2011 | Joanny |

FOREIGN PATENT DOCUMENTS

| EP | 0542979 | 12/1992 |
| FR | 2296426 | 7/1976 |
| FR | 2616068 | 12/1988 |
| FR | EP 0 542 979 B1 * | 5/1993 |
| GB | 1356097 | 6/1974 |
| WO | 0122943 A | 4/2001 |
| WO | 2004/105778 | 12/2004 |
| WO | 2005049053 | 6/2005 |
| WO | 2005091872 | 10/2005 |

OTHER PUBLICATIONS

English translation (complete) of EP 0542979.
U.S. Appl. No. 12/993,683, filed Nov. 19, 2010.
Office Action mailed Nov. 5, 2012 for U.S. Appl. No. 12/993,683, including lists of information considered and Examiner search history.
Denda, M., "New strategies to improve skin barrier homeostatis", Advanced Drug Delivery Reviews, 54 Suppl.1, S123-S130, 2002.
Denda, M. et al., "Negative Electric Potential Induces Alteration of Ion Gradient and Lamellar Body Secretion in the Epidermis, and Accelerates Skin Barrier Recovery After Barrier Disruption", The Journal of Investigative Dermatology, vol. 118(1), pp. 65-72, 2002.
Roth, P. et al., 'Intestinal Absorption of Magnesium in Man', International Journal of Applied Radiation and Isotopes, vol. 30, pp. 523-526, 1979.
Berthelot, A. et al., 'Le Magnésium' pp. 27-30, John Libbey Eurotext editor (collection Pathology Science Formation), Dec. 2004 (English abstract attached).
Vippagunta et al, Advanced Drug Reviews, vol. 48, Abstract 2001.
Office Action dated Oct. 28, 2008 for U.S. Appl. No. 11/286,192, including lists of references cited by examiner and applicant.
Seelig, Journal of the American College of Nutrition, vol. 13, No. 5, Abstract, 1994.
Walker et al., Phytotherapy, vol. 16, pp. 48-54, 2002.
Galinksy et al, "Basic Pharmacokinetics and Pharmacodynamics" in Remington: The Science and Practice of Pharmacy (Baltimore, Lippencott Williams & Wilkins 2006), p. 1171.
Morissette et al, Advanced Drug Delivery Reviews, vol. 56, pp. 275-300, 2004.
International Search Report for PCT/FR2009/000586.
International Search Report for PCT/FR2009/000585.
Written Opinion from parent PCT application No. PCT/FR2009/000585.

* cited by examiner

Primary Examiner — Michael G Hartley
Assistant Examiner — Micah-Paul Young
(74) Attorney, Agent, or Firm — J-Tek Law PLLC; Jeffrey D. Tekanic

(57) ABSTRACT

A tablet for oral administration comprises a matrix of progressive and continuous released magnesium. For the administration of 90 to 110 parts by weight of magnesium, the matrix comprises 180 to 190 parts by weight of hydroxypropylmethylcellulose, 19.8 to 22.2 parts by weight of glyceryl behenate, 10 to 12 parts by weight of lactose and 10 to 12 parts by weight of colloidal silica. A non-enteric protective coating that slows down the gastric dissolution of the magnesium may comprise 15 to 75 parts by weight of shellac, cellulose ether or a mixture thereof. The tablet may be administered to patients in need thereof.

19 Claims, No Drawings

USE OF A MATRIX FOR ORALLY ADMINISTERING SUSTAINED RELEASE MAGNESIUM, AND COMPOSITION CONTAINING SAID MATRIX

CROSS-REFERENCE

This application is the US national stage of International Patent Application No. PCT/FR2009/000585 filed on May 20, 2009, which claims priority to French Patent Application No. 0802702 filed on May 20, 2008.

FIELD OF THE INVENTION

The present invention relates to a new use of a matrix for oral administration of magnesium in tablet form, with sustained release, for improving the bioavailability of magnesium through a progressive and continuous dissolution all along the gastrointestinal tract. It also relates to a new industrial product, which is a composition comprising magnesium with sustained release, especially as a food supplement, which is in tablet form.

PRIOR ART

From "Le magnésium" by Berthelot A., Arnaud M., and Reba A., pages 27-30, John Libbey Eurotext ('Pathologie Science Formation' collection), December 2004, it is known (i) that it is difficult to assay magnesium in the body; (ii) that, for evaluating the metabolism, it is usual to measure the level of magnesium in the plasma, which, however, is not always a good reflection of the overall magnesium pool, because approximately 12% to 23% by weight of the magnesium content in the body can be rapidly exchanged, particularly with sodium, potassium, and calcium; and (iii) that the region of the ileum is the most favorable site for the passage of the magnesium through the intestinal wall.

From the article 'Intestinal Absorption of Magnesium in Man' in particular, by Roth P. and Werner E., International Journal of Applied Radiation and Isotopes, 1979:30, 523-526, it is known from the oral administration of the isotope $^{28}$Mg to humans that the bioavailability, expressed in the form of percentage of magnesium absorbed relative to the amount by weight of magnesium administered, decreases when the dosage of magnesium increases. In this regard, see Table 1 of said article, which is summarized below:

Summary of Table 1 from Roth P. et al.

| Oral dosage of Mg (mmol) | Average fraction absorbed (%) |
|---|---|
| 0.3 | 0.70 |
| 1.3 | 0.48 |
| 4.2 | 0.29 |
| 12.5 | 0.20 |
| 41.7 | 0.14 |

It is known, particularly from the publications WO 01/22943 A, U.S. Pat. No. 6,887,492 B, U.S. Pat. No. 5,849,338 A, and GB 1356097 A, which illustrate the prior art, that in the past there have already been technical solutions proposed with the aim of supplying delayed-release magnesium (i.e., with postponed, slow or reduced release over time).

GB Patent 1356097 A proposes a slow-release polyelectrolyte composition for the continuous substitution of mineral salts lost due to bodily stress, heavy perspiration, and the use of diuretics. This composition takes the form of a matrix containing, in the form of salts, 5 to 80 parts by weight of Ca, 5 to 40 parts by weight of Mg, 2 to 20 parts by weight of K, and no Na or less than 20 parts by weight of Na. This patent is of no interest for the release of magnesium alone, and, moreover, does not describe the means employed for obtaining the desired slow and sustained release.

U.S. Pat. No. 5,849,338 A recommends a delayed-release composition for the treatment of vasoconstriction, comprising a plurality of active ingredients in combination, particularly the following combination:
  MgO and/or at least one Mg salt,
  a substance from the family of vitamin E,
  ascorbic acid or an ascorbate,
  selenium,
  folic acid or a folate, and
  a hormone, melatonin;
and, as an excipient, a delayed-release matrix based on cellulosic polymers or on film coatings which are resistant to acids. This patent neither describes nor suggests the means employed in accordance with the invention for the slow and sustained release of the magnesium.

U.S. Pat. No. 6,887,492 B provides for a unit-dosage form tablet or capsule composition comprising:
  at least one magnesium compound which releases Mg within the intestine, and which is housed in a core having an enteric coating, and
  a peripheral layer containing calcium that can be released in the stomach and that surrounds said enteric coating.

Published International patent application WO 01/22943 A proposes incorporating a hygroscopic solid, liquid or gaseous active substance [such as carnitine (especially L-carnitine, DL-carnitine or acetyl-L-carnitine)] into a magnesium-compound cement ('Sorel cement') to give a delayed-release form which releases said active substance and magnesium. Sorel cement, obtained from the reaction:

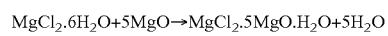

followed by reduction through dehydration, is a mixture of magnesium oxychlorides having the structure:

wherein a is an integer having the value of 1, 2, 3, 4 or 5, the predominant compounds by weight in this mixture being those in which a=2 and a=3.

Furthermore, with regard to oral compositions of magnesium with sustained release, the known documents include granted European patent EP 0542979 B and, in particular, the publication of International patent application WO 2004/105778 A.

EP Patent 0542979 B is directed to a therapeutic composition which is useful with respect to magnesium deficiencies and is intended to provide sustained release of the magnesium it contains, in the form of $Mg^{2+}$, which can be absorbed in the intestines, in order to supplement at least 6 mg/kg of the daily supply of magnesium for a human, said composition being characterized in that it comprises a mixture comprising, in combination with a physiologically acceptable excipient,
  (a) 4 to 14 parts by weight of magnesium, originating from a source consisting of MgO, $MgCl_2$, and hydrates of formula $MgCl_2.n(H_2O)$ where n is an integral or fractional number greater than 0 and less than or equal to 6,
  (b) 6 to 13 parts by weight of a hydrophilic polymer when the Mg source is MgO, or 10 to 30 parts by weight of a hydrophobic substance selected from the group consisting of physiologically-acceptable hydrophobic polymers, fatty acid esters, and mixtures thereof when the Mg source is other than MgO, and (c) 6 to 16 parts by weight of an inert filler acting as a solid diluent and selected in particular from the group consisting of lactose, alkali metal and alkaline earth metal phosphates, and mixtures thereof, the amount of Mg in said mixture being between 5% and 60% by weight relative to the weight of said mixture.

The composition according to EP 0542979 B is generally coated in a shell, which is an enteric film coating, and takes the form of a tablet containing 50 mg of magnesium intended to be taken once or twice daily.

The published International patent application WO 2004/105778 A proposes a combination which is useful in cosmetology, in therapeutics and/or in the field of nutrition, in particular for counteracting stress conditions, and which is characterized in that it consists of (α) a sustained-release magnesium preparation (I) comprising, in combination with a physiologically acceptable excipient, a mixture:
(A) of magnesium originating from a magnesium source consisting of MgO, $MgCl_2$, and hydrates of formula $MgCl_2.n(H_2O)$ where n is an integral or fractional number greater than 0 and less than or equal to 6,
(B) at least one substance selected from B1 and B2 or a combination thereof:
(B1) a hydrophilic polymer which is a cellulose derivative, and/or
(B2) a hydrophobic substance forming part of the family of esters of fatty acids with polyols, and
(C) an inert filler acting as solid diluent, in particular lactose,
the amount of Mg in said mixture being between 1% and 60% by weight relative to the weight of said mixture A+B+C; and (β) an active substance (Z) which is, in particular, an extract of a plant (such as valerian, balm, sea thyme, maritime pine bark, lime tree sapwood, cereal, apple, melon) or algae.

The preparation I and the substance Z may be administered orally, either simultaneously in a single unit or separately (especially in the context of a polytherapy) in two separate units.

The coating of preparation I or that of the single unit of the combination I+Z is carried out by means of an enteric film coating. In the form of a unit-dosage tablet (containing 100 mg of magnesium) to be taken once daily, the composition I is administered in the context of a polytherapy, or the mixture of I and Z is administered in the context of a single dosage.

The composition with the enteric coating according to EP 0542979 B, and the preparation I likewise with the enteric coating according to WO 2004/105778 A, give good results with respect to the sustained release of the magnesium from a tablet. However, said composition according to EP 0542979 B and said preparation I according to WO 2004/105778 A are barely satisfactory from the standpoint of the bioavailability of the magnesium.

SUMMARY OF THE INVENTION

A need exists to improve the bioavailability of the magnesium for progressive release over time. In particular, when the kinetics of the release of magnesium in vitro are assessed using the conventional system as follows:

dissolving with an acidic medium [advantageously 900 ml, according to the US Pharmacopoeia] of 0.1N HCl from time T=0 to time T=2 h (i.e. treatment corresponding approximately to the transit time in the stomach), then dissolving in a buffer [advantageously 900 ml] at a pH of 6.8 from time T=2 h to T=8 h [i.e. treatment corresponding approximately to the transit time in the small intestine (from T=2 h to T=4 h), then treatment corresponding approximately to the transit in the large intestine (from T=4 h to T=8 h)], it is observed that, when an enteric coating according to the composition of EP 0542979 B or according to preparation I of WO 2004/105778 A is used, the kinetics of release of $Mg^{2+}$ (ratio: amount in % by weight of Mg dissolved/time), which is substantially zero from T=0 to T=2 h, is too great during the interval from T=2 h to T=4 h, thereby reducing the bioavailability.

It has also been observed, surprisingly, that it is necessary for the dissolution (i) to start in the 'gastric' phase (from T=0 to T=2 h) with slowed down dissolution kinetics [the rate of dissolution (δ) of magnesium relative to the magnesium administered via the magnesium source preferably being less than or equal to 60%], so that (ii) Mg arrives in a drawn-out dose in the small intestine, where it begins to be absorbed with low kinetics (from T=2 h to T=4 h), on the one hand, and then (iii) Mg arrives at the 'large intestine' phase (from T=4 h to T=8 h), on the other hand.

The invention resides in particular in (1.) the preferential absorption of $Mg^{2+}$ in the ileum, the site of maximum absorption of Mg, and (2.) a slower and more progressive, programmed dissolution from the discharge from the stomach up to the large intestine.

According to the present invention, the release of magnesium in the form of $Mg^{2+}$ takes place continuously throughout the gastrointestinal tract, from the stomach to the large intestine, whereas the absorption of magnesium (still in the form of $Mg^{2+}$) takes place all along the intestinal tract from the duodenum to the large intestine, the absorption being at its maximum in the ileum (i.e. the last part of the small intestine).

According to a first aspect of the invention, a matrix is provided for oral administration, in tablet form, of magnesium with progressive release, said matrix having no enteric coating but having a protective coating that slows down or retards the gastric dissolution of the Mg, and said matrix, which forms a core comprised of a hydrophilic retardant (B1), a hydrophobic retardant (B2), an inert filler (C1) acting as diluent, and an inert filler (C2) acting as lubricant, being characterized in that it comprises, for the administration of (A) 90 to 110 parts by weight of magnesium, the following ingredients:

(B1) 180 to 190 parts by weight of hydroxypropylmethylcellulose, (B2) 19.8 to 22.2 parts by weight of glyceryl behenate, (C1) 10 to 12 parts by weight of lactose, and (C2) 10 to 12 parts by weight of colloidal silica.

The coating of the matrix (i.e. the coating of the uncoated tablet) is not enteric. It acts to protect the matrix, particularly during packing and storage, on the one hand, and it slows down the release of the magnesium in the stomach, on the other hand. It represents in general 15 to 75 parts by weight for a quantity of 90 to 110 parts by weight of Mg (i.e. approximately 1.3% to 7.5% by weight, relative to the weight of the matrix, in other words of the uncoated tablet).

The rate of dissolution (δ) of the magnesium (expressed in % relative to the total magnesium provided by the magnesium source) has been determined in vitro. The coated matrix, after 2 h in 0.1N HCl medium, preferably provides a dissolution rate δ of less than or equal to 60%.

When the aim is to assess the overall in vitro dissolution kinetics of a tablet, a conventional dissolution system (denoted "dissolution system A" here) is employed, first in a 0.1N HCl medium from T=0 to T=2 h, then in a buffer at pH 6.8 from T=2 h to T=8 h, in order to determine the cumulative amounts of dissolved active substance, in this case the magnesium, at the times T=2 h, T=4 h, T=6 h and T=8 h. These dissolution kinetics are determined at a temperature which may be from ambient temperature (15-25° C.) to 40° C. Since, in the present invention, the coated tablet and its constituents are all stable when stored at 40° C. for a number of months, the dissolution kinetics were measured herein at 40° C., according to convention, so as to be under temperature conditions substantially close to the temperature within the human body.

The coated tablet preferably exhibits a dissolution profile such that at T=2 h, δ≦60%, preferably 20%≦δ≦60%, and more preferably 25%≦δ≦58%;

at T=4 h, δ≦85%, preferably 40%≦δ≦85%, and more preferably 45%≦δ≦82%;

at T=6 h, δ≦98%, preferably 60%≦δ≦98%, and more preferably 80%≦δ≦95%; and at T=8 h, δ≦100%, preferably 90%≦δ≦100%, and more preferably 95%≦δ≦99.9%.

According to another aspect of the invention, a composition is provided for oral administration of magnesium, in tablet form, with progressive release, said composition being characterized in that it is composed of a matrix forming a core and comprising, in a mixture, (A) an amount of $MgCl_2.9/2H_2O$ providing 90 to 110 parts by weight of magnesium, (B1) 180 to 190 parts by weight of hydroxypropylmethylcellulose, (B2) 19.8 to 22.2 parts by weight of glyceryl behenate, (C1) 10 to 12 parts by weight of lactose, and (C2) 10 to 12 parts by weight of colloidal silica; and a protective coating that slows down the release of magnesium in the stomach, and that is not enteric.

According to yet another aspect, a new use is provided of a composition according to the invention, characterized in that said composition is employed for producing a product in the form of a tablet intended for progressive-release use of magnesium as a food supplement.

DETAILED DESCRIPTION OF THE INVENTION

Since magnesium is absorbed all along the intestinal tract, from the duodenum to the large intestine, and is optimum at the ileum (i.e., the last part of the small intestine), the transit time varying with the type of meal, and since, in the aforementioned dissolution system A, at T=2 h there remains Mg administered that is not yet dissolved, according to the invention, an optimally absorbable amount of the magnesium released (in the form of $Mg^{2+}$) reaches the ileum, to cross the intestinal wall.

According to the present teachings, the dissolution kinetics are preferably such that the release of Mg takes place (i) relatively slowly and (ii) progressively from the 'gastric' phase onward. These kinetics were determined using the dissolution system A and are given in Table I below for tablets according to the invention (Ex. 1-Ex. 5, Ex. 7 and Ex. 11-Ex. 12) and for comparative tablets (CP 1 to CP 5). The preferred dissolution kinetics involve particular values regarding dissolution in the stomach (thereby prohibiting an enteric film-coating) on the one hand, and in the small intestine on the other hand.

The above-indicated amounts by weight of A, B1, B2, C1, and C2 provide for optimum bioavailability of magnesium. These amounts provide an amount of dissolved magnesium, at the exiting of the 'small intestine' phase (i.e. at T=4 h), at 40° C., which is generally lower than or similar to that in the prior art. Contrary to the prior art, however, the dissolution profile of the coated matrix preferably exhibits kinetics which have a relatively shallow slope in the 'small intestine' phase (see in particular the kinetics of Ex. 11 and Ex. 12 in said Table I), The matrix according to the invention and its coating do not involve any product which is prohibited by European and international regulations in relation to food supplements. In particular, said matrix and said coating are free from PVC and polyvinylpyrrolidone.

The amount of Mg dissolved at T=4 h (40% to 85% of the Mg administered, and preferably 45% to 82% of the Mg administered) is substantial, to give a matrix which is suitable for (i) tableting, (ii) progressive and continuous release as desired, and especially (iii) an optimum bioavailability of magnesium. This amount results in an appropriate release within the ileum, on the one hand, and also leads, in relation to the amount of Mg dissolved in the 'gastric' phase, to a slower and more progressive release, which promotes absorption that is better adapted to the physiological mechanism of the passage of magnesium through the intestinal wall, on the other hand.

Substance B1 is hydroxypropylmethylcellulose (HPMC). It is used here in a grade which is suitable for pharmaceutical or food use.

Substance B2 is glyceryl behenate, which is a mixture comprised essentially of the monoglyceride and diglyceride of behenic acid (alternative nomenclature: 'mono-diglyceride behenate') and is known under the European name of additive E471. Substance B2 is also used here in a grade which is suitable for pharmaceutical or food use.

According to a preferred aspect of the present teachings, the B1/B2 weight ratio is preferably between 180/22.2=8.1/1 and 190/19.8=9.6/1. Advantageously, it is recommended that said weight ratio is between 8.5/1 and 9.3/1. The B1/B2 weight ratio will preferably be between 8.7/1 and 9.2/1, for example: 8.8/1 or 9/1 or else 9.15/1.

The lactose, component C1, is advantageously anhydrous. Similarly, the colloidal silica, component C2, is advantageously anhydrous. In practice it tends to be preferred for the C1/C2 weight ratio in the matrix of the invention to be close to 1/1 and better still equal to 1/1.

The coating of the invention is not enteric. It comprises a film coating which acts (i) to protect the components of the uncoated tablet with respect to the exterior, particularly with respect to impact, and especially (ii) to slow down the dissolution of Mg in the 'gastric' phase. This film coating may be produced as a single layer, two layers, or even three layers. To limit the manufacturing costs, it is possible for it to be a single layer. However, a two-layer coating is recommended advantageously, for better control of the dissolution of Mg. As indicated above, the coating of the matrix represents, in general, 15 to 75 parts by weight for a magnesium source supplying 90 to 110 parts by weight of Mg (i.e. approximately 1.3% to 7.5% by weight relative to the weight of the matrix). Preferably it will represent 15 to 70 parts by weight, and better still 15 to 45 parts by weight, per 90 to 110 parts by weight of Mg.

The substances recommended here for the coating are shellac and film-forming cellulose ethers, such as alkylcelluloses, which are, more particularly, the mixtures of HPMC and hydroxypropylcellulose (HPC) that are sold, in particular, under the names NUTRATERIC® and OPADRY®. It is also possible to consider a coating comprised of a first layer of shellac and an outer layer made from a mixture of alkylcelluloses.

In practice, a coating is recommended which is
(a) a single-layer film coating of shellac (used at 50% by weight in ethanol, the solvent being removed during the film coating), or
(b) a two-layer film coating, each layer comprising a substance selected from shellac, cellulose ethers (especially HPMC and HPC), and mixtures thereof.

When a two-layer coating is used, the first layer (or inner layer) represents, in general, 0.5% to 4% by weight relative to the weight of the matrix, and the second layer (or outer layer) represents, in general, 0.5% to 3.5% by weight relative to the weight of said matrix, the combination of the two said layers representing 1.3% to 7.5% by weight relative to the weight of said matrix.

The Mg source is comprised, according to the invention, of MgO, $MgCl_2$, and hydrates of the formula $MgCl_2 \cdot n(H_2O)$, where n is an integral or fractional number greater than 0 and less than or equal to 6. The salts of Mg with organic acids are generally not suitable here (in particular when they are salts of fatty acids). The reason is that (a) the weight percentage of magnesium in these salts goes down as the molecular mass goes up, and (b) consequently, these salts lead to tablets whose size and mass are such that it becomes difficult to swallow them. The preferred source according to the invention is a hydrate, namely $MgCl_2 \cdot 9/2H_2O$.

In a preferred embodiment of the present teachings, a composition is provided, in a film-coated tablet form, which releases magnesium progressively and continuously. This composition preferably comprises:
a matrix constituting a core comprising
(A) 90 to 110 parts by weight of magnesium, the source of magnesium preferably being $MgCl_2 \cdot 9/2H_2O$,
(B1) 180 to 190 parts by weight of hydroxypropylmethylcellulose,
(B2) 19.8 to 22.2 parts by weight of glyceryl behenate,
(C1) 10 to 12 parts by weight of lactose, and
(C2) 10 to 12 parts by weight of colloidal silica; and
a film coating of
(D) 15 to 45 parts by weight of a substance selected from shellac, cellulose ethers (especially HPMC and HPC), and mixtures thereof.

It is recommended that the composition according to the invention is kept at a temperature of less than 40° C., and preferably at a temperature less than or equal to 25° C.

This composition is particularly useful as a food supplement. It acts advantageously, moreover, as a cosmetic for (i) moisturizing the skin, and/or (ii) treating or preventing stress of the skin. The cosmetic advantage of the Mg provided by this composition in the skin may be evaluated as follows:
by measuring the electrical impedance of the skin (expressed in Ω) or its inverse, the conductance (expressed in S), the moisture level in the skin being inversely proportional to the impedance and proportional to the conductance; in this regard, see the methods described by Kalia Y. et al., *Biophys.* 11996; 71(5):2692-2700, Kalia Y. et al., *J. Pharm. Sci.* 1998; 87(12):1508-1811, Curdy C. et al., *AAPS Pharm. Sci.* 2000; 2(3):E23, and Clar E. J. et al., *J. Cosm. Chem.* 1975; 26:337-357; and/or
by the analysis of human skin explants maintained under survival conditions.

Moreover, attention is drawn to the fact that WO 2009/150324 A1 is directed to a specific use of said composition in cosmetology.

Other advantages and features of the invention will be appreciated more fully from reading below of working examples ('Ex') and comparative examples ('CP'), on the one hand, and of results of comparative tests, on the other hand. All of these elements, of course, are not limiting, but instead are given by way of illustration.

The tests relating to determination of the dissolution kinetics of Mg were carried out at 40° C. in vitro using the aforementioned system A: 0.1N HCl medium from T=0 to T=2 h, then buffer medium at pH 6.8 from T=2 h to T=8 h.

Example 1

Tablets were prepared (with a magnesium dosage of 100 mg) having the following formulation (the B1/B2 weight ratio being 9.15/1), and Amount/tab representing the amount (expressed in mg) of each constituent of the tablet.

| Constituents | Amount/tab (mg) |
| --- | --- |
| Core: | |
| $MgCl_2 \cdot 9/2H_2O$ | 725.0 |
| HPMC | 183.0 |
| behenate mono-diglyceride | 20.0 |
| anhydrous lactose | 11.0 |
| anhydrous colloidal silica | 11.0 |
| Film coating: | |
| shellac | 39.6 |
| Total: | 989.60 |

For the dissolution profile of Ex. 1, see Table I below.

Example 2

Tablets were prepared (with a magnesium dosage of 100 mg) having the following formulation (the B1/B2 weight ratio being 9.35/1).

| Constituents | Amount/tab (mg) |
| --- | --- |
| Core: | |
| $MgCl_2 \cdot 9/2H_2O$ | 725.0 |
| HPMC | 185.2 |
| behenate mono-diglyceride | 19.8 |
| anhydrous lactose | 11.0 |
| anhydous colloidal silica | 11.0 |
| Film coating: | |
| shellac | 39.42 |
| Patent Blue | 0.03 |
| Total: | 992.45 |

For the dissolution profile of Ex. 2, see Table I below.

Example 3

Tablets were prepared (with a magnesium dosage of 100 mg) having the following formulation (the B1/B2 weight ratio being 9.25/1).

| Constituents | Amount/tab (mg) |
|---|---|
| Core: | |
| $MgCl_2 \cdot 9/2H_2O$ | 725.0 |
| HPMC | 185.0 |
| behenate mono-diglyceride | 20.0 |
| anhydrous lactose | 11.0 |
| anhydrous colloidal silica | 11.0 |
| Film coating: | |
| shellac | 39.6 |
| Total: | 991.60 |

For the dissolution profile of Ex. 3, see Table I below.

Example 4

Tablets were prepared (with a magnesium dosage of 100 mg) having the following formulation, in accordance with the methods above (the B1/B2 weight ratio being 9.15/1).

| Constituents | Amount/tab (mg) |
|---|---|
| Core: | |
| $MgCl_2 \cdot 9/2H_2O$ | 725.0 |
| HPMC | 183.0 |
| behenate mono-diglyceride | 20.0 |
| anhydrous lactose | 11.0 |
| anhydrous colloidal silica | 11.0 |
| Film coating 1: | |
| shellac | 24.17 |
| Film coating 2: | |
| 1/3 w/w HPMC/HPC mixture | 17.514 |
| Patent Blue | 0.016 |
| Total: | 991.70 |

For the dissolution profile of Ex. 4, see Table I below.

Example 5

Tablets were prepared (with a magnesium dosage of 100 mg) having the following formulation (the B1/B2 weight ratio being 9.15/1).

| Constituents | Amount/tab (mg) |
|---|---|
| Core: | |
| $MgCl_2 \cdot 9/2H_2O$ | 725.0 |
| HPMC | 183.0 |
| behenate mono-diglyceride | 20.0 |
| anhydrous lactose | 11.0 |
| anhydrous colloidal silica | 11.0 |
| Film coating: | |
| 1st layer: shellac | 19.8 |
| 2nd (outer) layer: 1/4 w/w HPMC/HPC mixture | 19.8 |
| Total: | 989.60 |

For the dissolution profile of Ex. 5, see Table I below.

Example 6

In accordance with the terms of Example 5, tablets were prepared containing 50 mg of magnesium and an amount of each constituent which is half the amount of the equivalent constituent in said Ex. 5.

Example 7

Tablets were prepared (with a magnesium dosage of 100 mg) having the following formulation (the B1/B2 weight ratio being 9.15/1).

| Constituents | Amount/tab (mg) |
|---|---|
| Core: | |
| $MgCl_2 \cdot 9/2H_2O$ | 725.0 |
| HPMC | 183.0 |
| behenate mono-diglyceride | 20.0 |
| anhydrous lactose | 11.0 |
| anhydrous colloidal silica | 11.0 |
| Film coating: | |
| 1st (inner) layer: 1/3 w/w HPMC/HPC | 19.8 |
| 2nd (outer) layer: 1/4 w/w HPMC/HPC mixture | 19.8 |
| Total: | 989.60 |

For the dissolution profile of Ex. 7, see Table I below.

Example 8

In accordance with the terms of Example 7, tablets were prepared containing 50 mg of magnesium and an amount of each constituent which is half the amount of the equivalent constituent in said Ex. 7.

Example 9

Tablets were prepared (with a magnesium dosage of 100 mg) having the following formulation (the B1/B2 weight ratio being 8.8/1).

| Constituents | Amount/tab (mg) |
|---|---|
| Core: | |
| $MgCl_2 \cdot 9/2H_2O$ | 725.0 |
| HPMC | 190.0 |
| behenate mono-diglyceride | 21.5 |
| anhydrous lactose | 10.0 |
| anhydrous colloidal silica | 10.0 |
| pyridoxine hydrochloride | 6.0 |
| Film coating: | |
| shellac | 40.0 |
| Total: | 1003.0 |

Example 10

Tablets were prepared (with a magnesium dosage of 50 mg) having the following formulation (the B1/B2 weight ratio being 9.15/1).

| Constituents | Amount/tab (mg) |
|---|---|
| Core: | |
| $MgCl_2 \cdot 9/2H_2O$ | 362.50 |
| HPMC | 91.50 |
| behenate mono-diglyceride | 10.00 |
| anhydrous lactose | 5.50 |
| anhydrous colloidal silica | 5.50 |
| Film coating 1: | |
| shellac (OPAGLOS ® NA715G, product sold by the Colorcon company) | 1.3 to 2.2%* |
| Film coating 2: | |
| 1/3 w/w HPMC/HPC mixture (OPADRY ® VMS, product sold by the Colorcon company) | 1.1 to 1.6%* |
| Yellow 20A38069 | 0.008 |

Note
*percentage by weight relative to the weight of the uncoated tablet.

Example 11

Tablets were prepared (with a magnesium dosage of 50 mg) having the following formulation (the B1/B2 weight ratio being 9.15/1).

| Constituents | Amount/tab (mg) |
|---|---|
| Core: | |
| $MgCl_2 \cdot 9/2H_2O$ | 362.50 |
| HPMC | 91.50 |
| behenate mono-diglyceride | 10.00 |
| anhydrous lactose | 5.50 |
| anhydrous colloidal silica | 5.50 |
| Film coating: | |
| shellac (OPAGLOS ® NA715G, product sold by the Colorcon company) | 1.7%* |

Note
*percentage by weight relative to the weight of the uncoated tablet.

For the dissolution profile of Ex. 11, see Table I below.

Example 12

Tablets were prepared (with a magnesium dosage of 50 mg) having the following formulation (the B1/B2 weight ratio being 9.15/1).

| Constituents | Amount/tab (mg) |
|---|---|
| Core: | |
| $MgCl_2 \cdot 9/2H_2O$ | 362.50 |
| HPMC | 91.50 |
| behenate mono-diglyceride | 10.00 |
| anhydrous lactose | 5.50 |
| anhydrous colloidal silica | 5.50 |
| Film coating 1: | |
| shellac (OPAGLOS ® NA715G, product sold by the Colorcon company) | 1.7* |
| Film coating 2: | |
| 1/3 w/w HPMC/HPC mixture (OPADRY ® VMS, product sold by the Colorcon company) | 0.5%* |

Note
*percentage by weight relative to the weight of the uncoated tablet.

For the dissolution profile of Ex. 12, see Table I below.

Comparative Example CP 1

The present comparative example corresponds to a product, in accordance with EP patent 0542979 B, of the enteric-coated tablet type (with a dosage of 100 mg of Mg), which was sold in Belgium in 1999 and then withdrawn from the market after a short time. Its composition is that below.

| Constituents | Amount/tab (mg) |
|---|---|
| Core: | |
| $MgCl_2 \cdot 6H_2O$ | 836.09 |
| HPMC | 120.00 |
| glycerol palmitostearate | 112.28 |
| anhydrous lactose | 52.60 |
| hydrated colloidal silica | 13.03 |
| Enteric film coating: | |
| cellulose acetophthalate | 96.00 |
| ethyl phthalate | 24.00 |
| Total: | 1254.00 |

For the dissolution profile of CP 1, see Table I below.

Comparative Example CP 2

990 mg tablets were prepared each according to the formulation of Example 2 of EP patent 0542979 B, with the difference that the enteric fatty acid ester film coating was replaced by a single-layer shellac coating as in Example 1 above. The formulation is as follows:

| Constituents | % (by weight) |
|---|---|
| Core: | |
| $MgCl_2 \cdot 9/2H_2O$ | 44.50 |
| pyridoxine hydrochloride | 3.00 |
| anhydrous lactose | 14.78 |
| PVC | 18.40 |
| anhydrous colloidal silica | 0.92 |
| Film coating: | |
| shellac | 18.40 |
| Total: | 100.00 |

For the dissolution profile of CP 2, see Table I below.

Comparative Example CP 3

Tablets were prepared according to the formulation below.

| Constituents | Amount/tab (mg) |
| --- | --- |
| Core: | |
| $MgCl_2 \cdot 6H_2O$ | 836.00 |
| HPMC | 102.91 |
| behenate mono-diglyceride | 100.00 |
| anhydrous lactose | 50.05 |
| anhydrous colloidal silica | 11.34 |
| Film coating: | |
| shellac | 40.0 |
| Total: | 1140.00 |

The dissolution kinetics are (a) virtually zero during the 'gastric' phase and (b) too rapid (too steep of a slope) during the 'small intestine' phase. The reason is that 1% of the Mg is dissolved at T=2 h, and 90% of the Mg is dissolved at T=4 h. See Table I below.

Comparative Example CP 4

Tablets having a unit mass of 990 mg, without film coating, were prepared according to the formulation below.

| Constituents | Amount/tab (mg) |
| --- | --- |
| Core: | |
| $MgCl_2 \cdot 9/2H_2O$ | 725.0 |
| behenate mono-diglyceride | 202.91 |
| anhydrous lactose | 31.09 |
| anhydrous colloidal silica | 11.00 |
| Total: | 990.00 |

The dissolution kinetics are (a) zero during the 'gastric' phase and (b) too rapid (too steep of a slope) during the 'small intestine' phase. The reason is that 0% of the Mg is dissolved at T=2 h, and 80% of the Mg is dissolved at T=4 h. See Table I below.

Comparative Example CP 5

Tablets were prepared according to the formulation below.

| Constituents | Amount/tab (mg) |
| --- | --- |
| Core: | |
| $MgCl_2 \cdot 9/2H_2O$ | 725.0 |
| HPMC | 153.0 |
| behenate mono-diglyceride | 50.0 |
| anhydrous lactose | 11.0 |
| anhydrous colloidal silica | 11.0 |
| Film coating: | |
| 1st layer: shellac | 19.8 |
| 2nd (external) layer: 1/4 w/w HPMC/HPC mixture | 19.8 |
| Total: | 989.60 |

The dissolution kinetics are too low at the start: 15% of the Mg present is dissolved at T=2 h. See Table I below.

Comparative Tests I

Comparative tests were undertaken in order to determine the profile of the dissolution kinetics of the Mg present in the tablets of Ex. 1-Ex. 5, Ex. 7, Ex. 11-Ex. 12, and CP 1-CP 5. The results obtained, already discussed above, have been set out in Table I below.

Comparative Tests II

Tests were carried out on groups, each including 5 healthy human subjects, at one group per test tablet. In order to have groups of the same type, in which the subjects have approximately the same volume of blood, groups of subjects were selected with the same sex, the same age ±1 year, the same body weight ±1 kg, and the same height ±1 cm.

The groups of subjects were administered one tablet of Ex. 1, Ex. 5, Ex. 7, CP 1, CP 2 or CP 5, respectively, each morning for 14 days [the steady state is generally attained after 10 days].

On day 15, at time T=0, 10 milliliters of blood are taken from each subject and one tablet of Ex. 1, Ex. 5, Ex. 7, CP 1, CP 2 or CP 5, respectively, is administered, and then the plasma is collected for measurement of the plasma magnesium level by atomic absorption spectrometry (AAS).

At time T=8 h, 10 milliliters of blood are taken again from each subject, and the plasma is collected for measurement of the plasma magnesium level by atomic absorption spectrometry.

The results obtained are set out in Table II, which is given below.

This magnesium assay is not a priori a method which is entirely relevant for assessing the intestinal absorption of magnesium, since $Mg^{2+}$ which passes through the intestinal wall is attached preferentially to or in other tissues, especially the bones and the erythrocytes, on the one hand, and undergoes exchange with $Na^+$, $K^+$, and $Ca^{2+}$, on the other hand. This measurement does, however, allow verification of the advantage of the particular dissolution kinetics of the invention. Said Table II shows in particular that the change in plasma magnesium level between T=0 and T=8 h is 0.09-0.10 mmol/l for the inventive tablets Ex. 1, Ex. 2, and Ex. 7, while it is 0.02-0.04 mmol/l for the comparative tablets CP 1, CP 2 and CP 5.

Miscellaneous

The preferred method of implementing the invention involves employing the tablets of Examples 7, 11, and 12. The recommended daily dosage of Mg is 50 mg (one dose of Ex. 11 or Ex. 12 in the morning) or 100 mg (one dose of Ex. 7 in the morning, or one dose of Ex. 11 or Ex. 12 in the morning and one in the evening).

As indicated in the aforementioned document WO 2004/105778 A, it is possible to recommend combinations of the composition according to the invention, in the tablet form, with another active substance, either for a single unit administration or for separate administration of the Mg and the other active substance.

In particular it is possible to incorporate a vitamin substance such as Vit. B3, Vit. B 12 and/or coenzyme Q10 (each vitamin substance being present at an appropriate dosage) either in the core of the tablet according to the invention, which contains $MgCl_2 \cdot 9/2H_2O$, or in another tablet which is free from Mg. In the adult male, said appropriate dosages, which are generally recommended per os, are 18 mg/d for Vit. B3, 1 μm/d for Vit. B12, and 30-40 mg/d for coenzyme Q10.

Recommendation may also be given to separate administration, with the composition according to the invention, in the tablet form, being administered orally, and the other active substance (which may be a source of $Zn^{2+}$ ions, or an extract of a plant or algae) being administered topically. The generally recommended dosage per os in the adult male is 15 mg/d for zinc.

As a variant, when administering a tablet containing Mg and another active substance which can be released primarily in the stomach, it is possible for said active substance to be either disposed at the periphery of the core or housed within the mass of said coating.

The plant extracts which are useful here include extracts of valerian, balm, sea thyme, maritime pine bark, cereal, apple, and melon, already referred to in the aforementioned patent application WO 2004/105778 A, and also extracts of maca, pomegranate, rice bran, sea buckthorn, and rhodiola. The plant extract here may be an essential oil, as for example essential oil of lavender or essential oil of neroli. Moreover, use may also be made of extracts of algae, as for example an extract of Klamath algae (*Aphanizomenon flos-aquae*), which is useful internally or externally according to the invention.

For illustration, a number of examples now follow of combinations ('CB') which can be used, in the adult male, with the oral progressive-release magnesium composition of the invention.

Combination CB 1

A tablet like that of Ex. 1 above is administered orally, with the difference that the tablet, in the mass of the film coating, contains 20-30 mg of $ZnCl_2$, for the care and maintenance of the skin.

Combination CB 2

A tablet according to Ex. 5 above, on the one hand, and a tablet containing 30 to 50 mg of pomegranate extract (fruit of the pomegranate tree, *Punica granatum*), on the other hand, are administered orally, for antioxidant use.

Combination CB 3

A tablet according to Ex. 6 above, on the one hand, and a tablet containing maca extract (*Lepidium meyenii*), on the other hand, are administered orally, to combat physical fatigue after effort (especially in sport) or mental fatigue.

Combination CB 4

A tablet according to Ex. 1 above, on the one hand, and a topical composition containing essential oil of lavender, on the other hand, are administered orally for use as a means of relaxation, in view of the muscle relaxant effect produced by the combination of the magnesium with progressive release of the essential oil of lavender.

TABLE I

Dissolution kinetics

| | Dissolution rate δ (cumulative % of Mg dissolved) | | | |
|---|---|---|---|---|
| | in 0.1N HCl | in buffer at pH 6.8 | | |
| | at T = 2 h | at T = 4 h | at T = 6 h | at T = 8 h |
| According to the invention | 20% ≦ δ ≦ 60% | 40% ≦ δ ≦ 85% | 60% ≦ δ ≦ 98% | 90% ≦ δ ≦ 100% |
| Ex. 1 | δ = 21% | δ = 41% | δ = 82% | δ = 98% |
| Ex. 2 | δ = 25% | δ = 45% | δ = 83% | δ = 97% |
| Ex. 3 | δ = 30% | δ = 50% | δ = 85% | δ = 98% |
| Ex. 4 | δ = 32% | δ = 52% | δ = 85% | δ = 98% |
| Ex. 5 | δ = 27% | δ = 46% | δ = 84% | δ = 99% |
| Ex. 7 | δ = 28% | δ = 47% | δ = 85% | δ = 99% |
| Ex. 11 | δ = 53% | δ = 82% | δ = 96% | δ = 99.9% |
| Ex. 12 | δ = 56% | δ = 87% | δ = 96% | δ = 99.9% |
| CP 1 | δ = 0% | δ = 80% | δ = 92% | δ = 99% |
| CP 2 | δ = 1% | δ = 81% | δ = 93% | δ = 99% |
| CP 3 | δ = 1% | δ = 90% | δ = 99% | δ = 99% |

TABLE I-continued

Dissolution kinetics

| | Dissolution rate δ (cumulative % of Mg dissolved) | | | |
|---|---|---|---|---|
| | in 0.1N HCl | in buffer at pH 6.8 | | |
| | at T = 2 h | at T = 4 h | at T = 6 h | at T = 8 h |
| According to the invention | 20% ≦ δ ≦ 60% | 40% ≦ δ ≦ 85% | 60% ≦ δ ≦ 98% | 90% ≦ δ ≦ 100% |
| CP 4 | δ = 0% | δ = 80% | δ = 91% | δ = 99% |
| CP 5 | δ = 15% | δ = 79% | δ = 94% | δ = 99% |

TABLE II

Plasma magnesium levels by AAS

| Tablets | Sex of subjects | Plasma Mg levels (mmol/l) | | |
|---|---|---|---|---|
| | | at T = 0 | at T = 8 h | change from T = 0 to T = 8 h |
| Ex. 1 | F | 0.95 | 1.04 | 0.09 |
| Ex. 5 | M | 1.00 | 1.10 | 0.10 |
| Ex. 7 | M | 1.02 | 1.12 | 0.10 |
| CP 1 | F | 0.92 | 0.94 | 0.02 |
| CP 2 | M | 0.98 | 1.00 | 0.02 |
| CP 5 | M | 0.93 | 0.97 | 0.04 |

The invention claimed is:

1. A composition for oral administration, in tablet form, of magnesium with progressive release, comprising:
   a matrix constituting a core comprising
      (A) 90 to 110 parts by weight of magnesium, the source of magnesium being $MgCl_2.9/2H_2O$,
      (B1) 180 to 190 parts by weight of hydroxypropylmethylcellulose,
      (B2) 19.8 to 22.2 parts by weight of glyceryl behenate,
      (C1) 10 to 12 parts by weight of lactose, and
      (C2) 10 to 12 parts by weight of colloidal silica; and
   a film coating of
      (D) 15 to 75 parts by weight of a substance selected from shellac, cellulose ethers and mixtures thereof,
      wherein the composition exhibits, in vitro after 2 h in a 0.1N HCl medium, a rate of dissolution (δ) of the magnesium comprised therein of greater than or equal to 20% and less than or equal to 60%.

2. The composition according to claim 1, wherein said coating is one of:
   (a) a single-layer film coating of shellac, and
   (b) a two-layer film coating, each layer comprising a substance selected from shellac, cellulose ethers and mixtures thereof.

3. The composition according to claim 1, wherein, by determination in vitro in accordance with a dissolution system comprising first treating said composition in a 0.1N HCl medium from T=0 to T=2 h, and then treating it in a buffer at pH 6.8 from T=2 h to T=8 h, the composition exhibits an Mg dissolution rate (δ), relative to the Mg administered, such that
   at T=4 h, δ is less than or equal to 85%;
   at T=6 h, δ is less than or equal to 98%; and
   at T=8 h, δ is less than or equal to 100%.

4. The composition according to claim 3, wherein the composition exhibits an Mg dissolution rate (δ), relative to the Mg administered, such that at T=4 h, δ is greater than or equal to 40%;
at T=6 h, δ is greater than or equal to 60%; and
at T=8 h, δ is greater than or equal to 90%.

5. The composition according to claim 4, wherein the composition exhibits an Mg dissolution rate (δ), relative to the Mg administered, such that at T=2 h, δ is between 25-58%;
at T=4 h, δ is between 45-82%;
at T=6 h, δ is between 80-95%; and
at T=8 h, δ is between 95-99.9%.

6. The composition according to claim 5, wherein the film coating comprises 15-45 parts by weight of a substance selected from shellac, cellulose ether and a mixture thereof.

7. The composition according to claim 6, wherein the cellulose ether is at least one of hydroxypropylmethylcellulose and hydroxypropylcellulose.

8. The composition according to claim 7, wherein the film coating is one of:

(a) a single-layer film coating of shellac, and
(b) a two-layer film coating, each layer comprising a substance selected from shellac, cellulose ethers and mixtures thereof.

9. A method comprising:

orally administering, in tablet form, a therapeutically or cosmetically effective amount of a progressive release magnesium composition to a patient in need thereof, wherein the composition comprises:

a matrix constituting a core containing, for administration of 90 to 110 parts by weight of magnesium, the source of magnesium being $MgCl_2 \cdot 9/2H_2O$, the following additional ingredients: 180 to 190 parts by weight of hydroxypropylmethylcellulose, 19.8 to 22.2 parts by weight of glyceryl behenate, 10 to 12 parts by weight of lactose and 10 to 12 parts by weight of colloidal silica, and a protective coating that slows down gastric dissolution of the magnesium, wherein the composition exhibits, in vitro after 2 h in a 0.1N HCl medium, a rate of dissolution (δ) of the magnesium comprised therein of greater than or equal to 20% and less than or equal to 60%.

10. The method according to claim 9, wherein the coating constitutes 1.3% to 7.5% by weight relative to the weight of the matrix.

11. The method according to claim 9, wherein the coating is one of:

(a) a single-layer film coating of shellac, and
(b) a two-layer film coating, each layer comprising a substance selected from shellac, cellulose ethers and mixtures thereof.

12. The method according to claim 9, wherein the composition is administered as a food supplement.

13. The method according to claim 9, wherein the composition is administered as a cosmetic for at least one of: moisturizing skin and treating or preventing stress of the skin.

14. A progressive release magnesium tablet for oral administration, comprising:

a matrix constituting a core containing a mixture of
90 to 110 parts by weight of magnesium, the source of magnesium being $MgCl_2 \cdot 9/2H_2O$,
180 to 190 parts by weight of hydroxypropylmethylcellulose,
19.8 to 22.2 parts by weight of glyceryl behenate,
10 to 12 parts by weight of lactose, and
10 to 12 parts by weight of colloidal silica; and a film coating containing 15 to 75 parts by weight of a substance selected from shellac, cellulose ethers and a mixture thereof, wherein the tablet exhibits, in vitro after 2 h in a 0.1N HCl medium, a rate of dissolution (δ) of the magnesium comprised therein of greater than or equal to 20% and less than or equal to 60%.

15. The tablet according to claim 14, wherein the coating is one of:

(a) a single-layer film coating of shellac, and
(b) a two-layer film coating, each layer comprising a substance selected from shellac, cellulose ether and a mixture thereof.

16. The tablet according to claim 15, wherein, by determination in vitro in accordance with a dissolution system comprising first treating said composition in a 0.1N HCl medium from T=0 to T=2 h, and then treating it in a buffer at pH 6.8 from T=2 h to T=8 h, the tablet exhibits an Mg dissolution rate (δ), relative to the Mg administered, such that:

at T=2 h, δ is between 25-58%;
at T=4 h, δ is between 45-82%;
at T=6 h, δ is between 80-95%; and
at T=8 h, δ is between 95-99.9%.

17. The tablet according to claim 14, wherein the coating comprises an inner layer comprised of shellac and an outer layer comprised of a mixture of alkylcelluloses.

18. The tablet according to claim 17, wherein the mixture of alkylcelluloses comprises hydroxypropylmethylcellulose and hydroxypropylcellulose.

19. The tablet according to claim 14, wherein the film coating is 15 to 45 parts by weight.

* * * * *